United States Patent
Wascher et al.

[11] Patent Number: 6,083,149
[45] Date of Patent: Jul. 4, 2000

[54] MAGNETIC FIELD DEVICE AND METHOD FOR INHIBITING ANGIOGENESIS AND RETARDING GROWTH RATES OF TUMORS IN MAMMALS

[75] Inventors: Rick R. Wascher, Rock Island; C. Douglas Williams, Signal Mountain; Floyd E. Bouldin, Murfreesboro, all of Tenn.

[73] Assignee: EMF Therapeutics, Inc., Chattanooga, Tenn.

[21] Appl. No.: 09/111,769

[22] Filed: Jul. 8, 1998

Related U.S. Application Data

[63] Continuation-in-part of application No. 08/955,604, Oct. 22, 1997.
[51] Int. Cl.[7] ............................. A61B 17/52; A61N 2/00
[52] U.S. Cl. ................................................................ 600/9
[58] Field of Search .................................. 600/9, 10, 11, 600/13

[56] References Cited

U.S. PATENT DOCUMENTS

| | | |
|---|---|---|
| Re. 32,947 | 6/1989 | Dormer et al. . |
| 96,044 | 10/1869 | Smith . |
| 703,989 | 7/1902 | Burry . |
| 770,433 | 9/1904 | Kinraide . |
| 781,448 | 1/1905 | McIntyre . |
| 2,102,790 | 12/1937 | Drollinger . |
| 3,570,476 | 3/1971 | Gregg . |
| 3,890,953 | 6/1975 | Kraus et al. . |
| 3,915,151 | 10/1975 | Kraus . |
| 4,066,065 | 1/1978 | Kraus . |
| 4,134,395 | 1/1979 | Davis . |
| 4,233,965 | 11/1980 | Fairbanks . |
| 4,303,636 | 12/1981 | Gordon . |
| 4,402,309 | 9/1983 | Harrison . |
| 4,622,952 | 11/1986 | Gordon . |
| 4,626,792 | 12/1986 | Liboff et al. . |
| 4,641,633 | 2/1987 | Delgado . |
| 4,674,482 | 6/1987 | Waltonen et al. . |
| 4,765,310 | 8/1988 | Deagle et al. . |
| 4,818,697 | 4/1989 | Liboff et al. . |
| 4,838,850 | 6/1989 | Rosengart . |
| 4,889,526 | 12/1989 | Rauscher et al. . |
| 4,932,951 | 6/1990 | Liboff et al. . |
| 4,940,453 | 7/1990 | Cadwell . |
| 4,993,413 | 2/1991 | McLeod et al. . |
| 4,994,015 | 2/1991 | Cadwell . |
| 5,000,178 | 3/1991 | Griffith . |

(List continued on next page.)

FOREIGN PATENT DOCUMENTS

| | | |
|---|---|---|
| 0 048 451 | 3/1982 | European Pat. Off. . |
| 0 181 053 | 5/1986 | European Pat. Off. . |
| 0371504 | 6/1990 | European Pat. Off. . |
| 23 53 959 | 5/1975 | Germany . |
| 196 00 744 | 7/1997 | Germany . |

OTHER PUBLICATIONS

Winet, H.; "The Role of Microvasculature in Normal and Perturbed Bone Healing as Revealed by Intravital Microscopy"; Bone, vol. 19, No. 1 Supplement, Jul. 1996, pp. 39S–79S.

(List continued on next page.)

*Primary Examiner*—Max Hindenburg
*Assistant Examiner*—Brian Szmal
*Attorney, Agent, or Firm*—Rick R. Wascher

[57] ABSTRACT

A magnetic field device and method for inhibiting angiogenesis and retarding growth rates of cancerous tumors present in mammals. The apparatus includes a frame, and a wire consisting of electrically conducting material. The wire is wrapped around the frame to form a coil. A source of AC current is connected to a transformer to vary the AC voltage. The AC current is passed through a bridge rectifier and then to the coil of wire enabling a DC rectified wave magnetic field to be produced therefrom. The method employs the use of an apparatus which is capable of producing a magnetic field of a particular nature which has been proven in animal studies to affect angiogenesis and retard the growth rate of cancerous tumors.

49 Claims, 11 Drawing Sheets

U.S. PATENT DOCUMENTS

| | | |
|---|---|---|
| 5,010,897 | 4/1991 | Leveen . |
| 5,014,699 | 5/1991 | Pollack et al. . |
| 5,030,196 | 7/1991 | Inoue . |
| 5,045,050 | 9/1991 | Liboff et al. ............................... 600/9 |
| 5,047,005 | 9/1991 | Cadwell . |
| 5,059,298 | 10/1991 | Liboff et al. . |
| 5,061,234 | 10/1991 | Chaney . |
| 5,066,272 | 11/1991 | Eaton et al. . |
| 5,067,940 | 11/1991 | Liboff et al. . |
| 5,077,934 | 1/1992 | Liboff et al. . |
| 5,078,674 | 1/1992 | Cadwell . |
| 5,084,003 | 1/1992 | Susic . |
| 5,085,626 | 2/1992 | Frey . |
| 5,085,627 | 2/1992 | Federov et al. . |
| 5,087,336 | 2/1992 | Liboff et al. . |
| 5,088,976 | 2/1992 | Liboff et al. . |
| 5,090,423 | 2/1992 | Matsuda et al. . |
| 5,100,373 | 3/1992 | Liboff et al. . |
| 5,106,361 | 4/1992 | Liboff et al. . |
| 5,116,304 | 5/1992 | Cadwell . |
| 5,123,898 | 6/1992 | Liboff et al. . |
| 5,131,904 | 7/1992 | Markoll . |
| 5,143,588 | 9/1992 | Liboff et al. . |
| 5,156,587 | 10/1992 | Montone . |
| 5,160,591 | 11/1992 | Liboff et al. . |
| 5,183,456 | 2/1993 | Liboff et al. ............................... 600/9 |
| 5,195,940 | 3/1993 | Baylink . |
| 5,211,622 | 5/1993 | Liboff et al. . |
| 5,215,633 | 6/1993 | Liboff et al. . |
| 5,215,642 | 6/1993 | Liboff et al. . |
| 5,224,922 | 7/1993 | Kurtz . |
| 5,267,939 | 12/1993 | Liboff et al. . |
| 5,269,745 | 12/1993 | Liboff et al. . |
| 5,269,746 | 12/1993 | Jacobson . |
| 5,290,409 | 3/1994 | Liboff et al. . |
| 5,312,321 | 5/1994 | Holcomb . |
| 5,312,534 | 5/1994 | Liboff et al. . |
| 5,314,400 | 5/1994 | Tsyb et al. . |
| 5,318,561 | 6/1994 | McLeod et al. . |
| 5,330,410 | 7/1994 | Baylink . |
| 5,344,384 | 9/1994 | Ostrow et al. . |
| 5,357,958 | 10/1994 | Kaufman . |
| 5,366,435 | 11/1994 | Jacobson . |
| 5,368,544 | 11/1994 | Tran et al. . |
| 5,387,176 | 2/1995 | Markoll . |
| 5,415,617 | 5/1995 | Kraus . |
| 5,437,600 | 8/1995 | Liboff et al. . |
| 5,441,495 | 8/1995 | Liboff et al. . |
| 5,453,073 | 9/1995 | Markoll . |
| 5,458,558 | 10/1995 | Liboff et al. . |
| 5,476,438 | 12/1995 | Edrich et al. . |
| 5,518,495 | 5/1996 | Kolt . |
| 5,518,496 | 5/1996 | McLeod et al. . |
| 5,525,949 | 6/1996 | Hanley et al. . |
| 5,541,563 | 7/1996 | Leupold . |
| 5,658,234 | 8/1997 | Dunlavy . |
| 5,665,049 | 9/1997 | Markoll . |
| 5,669,868 | 9/1997 | Markoll . |
| 5,880,661 | 3/1999 | Davidson et al. . |

OTHER PUBLICATIONS

Sersa et al; "Tumor Blood Flow Changes Induced by Application of Electric Pulses"; Abstract of the 4th EBEA Congress, Zagreb, Croatia, Nov. 19–21, 1998.

Yen–Patton etal; "Endothelial Cell Response to Pulsed Electromagnetic Fields:Stimulation of Growth Rate and Angiogenesis in Vitro"; Journal of Cellular Physiology 134:37–45 (1998).

Guterl, Fred; "Beauty and Magnets"; Discover Magazine, Mar. 1997 pp. 38–43.

O'Brien, Jim; "Revolutionary New Magnetic Therapy Kos Arthritis Pain", Your Health Magazine, Apr. 6, 1993, pp. 17–18.

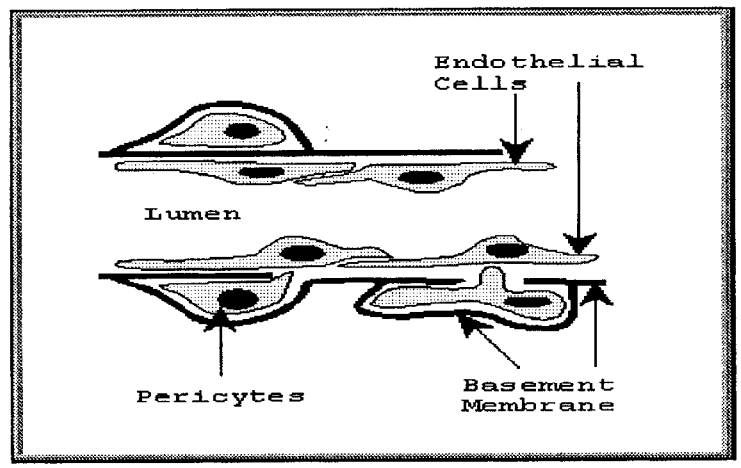
Background Fig. A
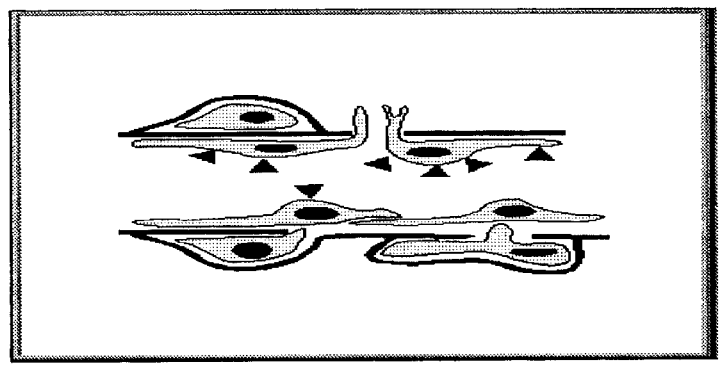
Background Fig. B
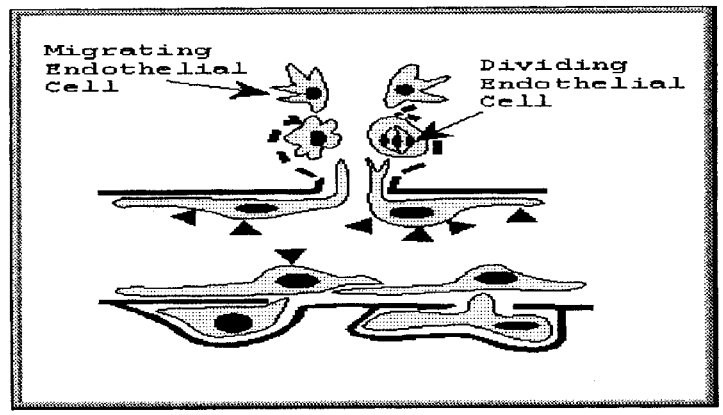
Background Fig. C

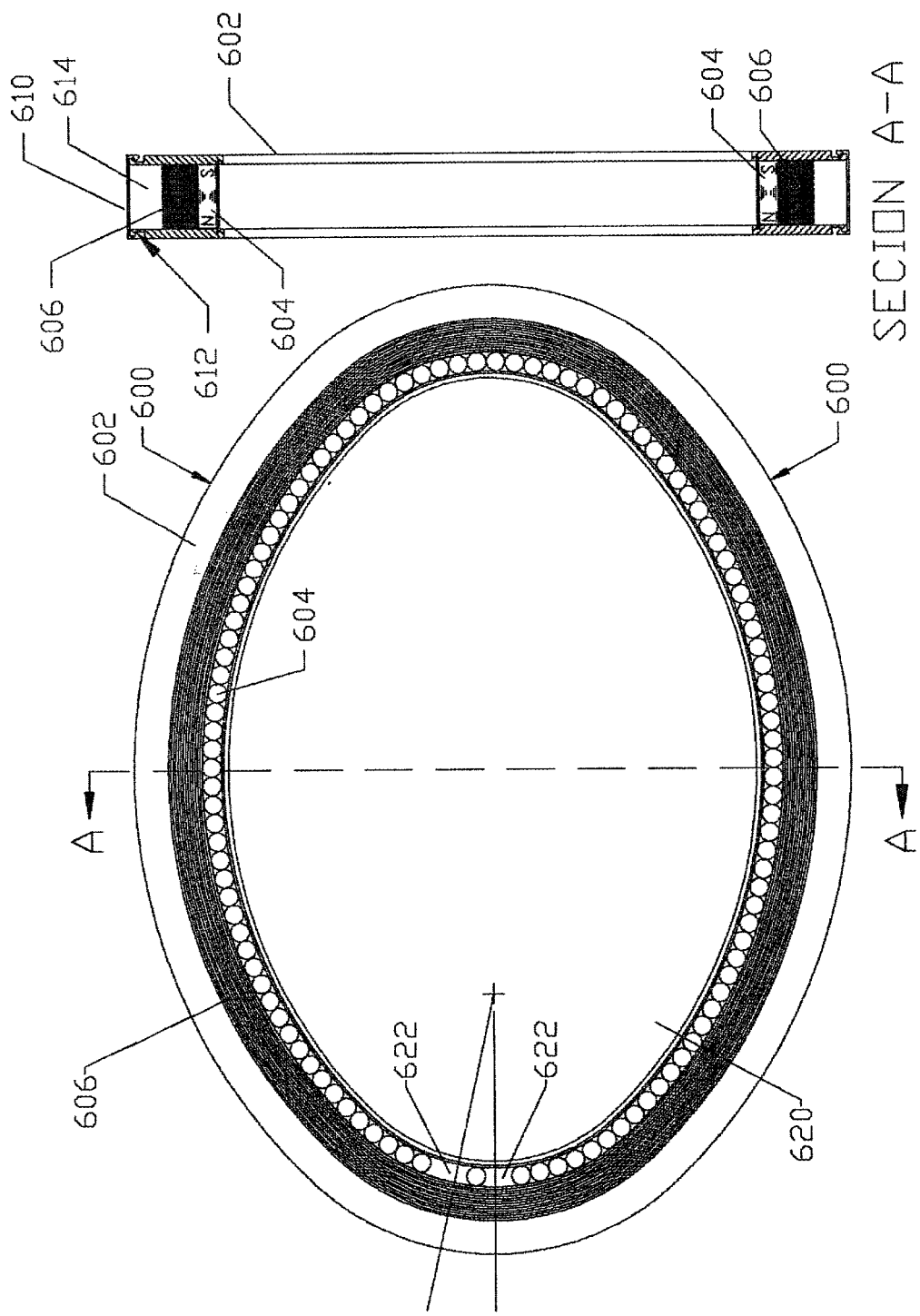

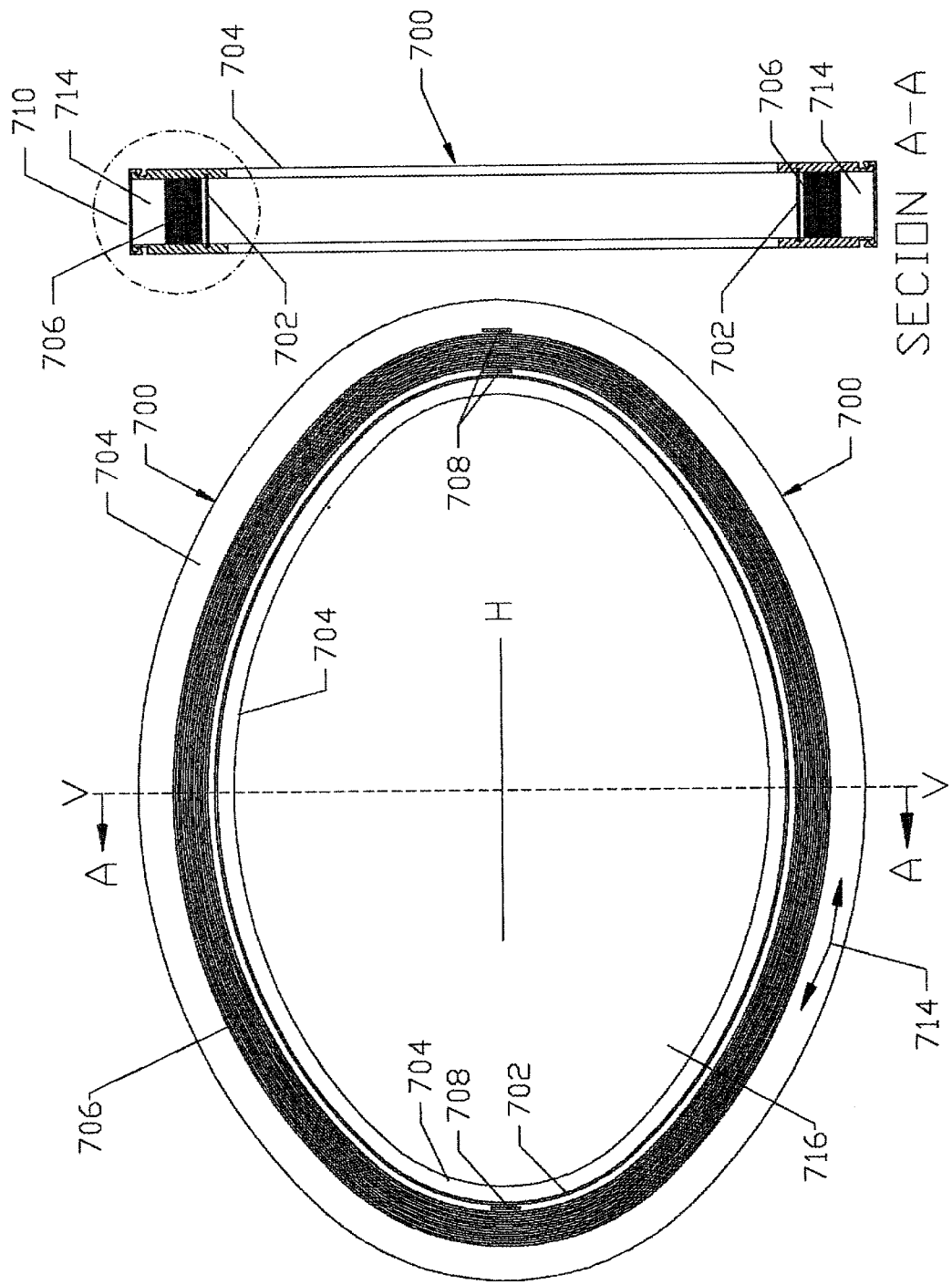

MAGNETIC FIELD DEVICE AND METHOD FOR INHIBITING ANGIOGENESIS AND RETARDING GROWTH RATES OF TUMORS IN MAMMALS

CROSS-REFERENCE TO OTHER APPLICATIONS

This application is a continuation-in-part of co-pending U.S. patent application Ser. No. 08/955,604 which was filed on Oct. 22, 1997.

BACKGROUND OF THE INVENTION

1. Field of the Invention

"Angiogenesis" may be defined as the formation, or the initiation, of the growth of blood carrying vessels or capillaries in a biological subject, particularly mammals.

The present invention and/or discovery (hereinafter collectively and individually referred to as the "invention" even though the subject matter of this application may comprise a discovery, an invention, or a combination thereof) is directed to the use of a device capable of producing a magnetic field or flux field found useful to inhibit angiogenesis in mammals. It is believed that the present invention was universally unknown to mankind prior to the time it became known the inventors hereof.

2. Description of the Related Art

In mature (non-growing) capillaries the vessel wall is composed of an endothelial cell lining, a basement membrane, and a layer of cells called pericytes which partially surround the endothelium. The pericytes are contained within the same basement membrane as the endothelial cells and occasionally make direct contact with them. (See Background Figure A).

With reference to Background Figure B, angiogenic factors (the black triangles) bind to endothelial cell receptors and initiate the sequence of angiogenesis. When the endothelial cells are stimulated to grow, they secrete proteases which digest the basement membrane surrounding the vessel. The junctions between endothelial cells are altered, cell projections pass through the space created and the newly formed sprout grows towards the source of the stimulus.

With reference to Background Figure C, continued capillary sprout growth is dependent upon several processes: the stimulus for growth (angiogenic factors, hypoxia, etc.) must be maintained; the endothelial cells must secrete the proteases required to break down the adjacent tissue; the cells themselves must be capable of movement/migration; and endothelial cell division must take place to provide the necessary number of cells (this takes place at a site behind the growth front of the sprout). Neighboring blind-ended sprouts then join together to form a capillary loop which later matures into a vessel like the one from which it arose.

The list of angiogenesis dependent diseases includes, but is not limited to the following: Angiofibroma which is an abnormal formation of blood vessels which are prone to bleeding; Neovascular Glaucoma which is an abnormal growth of blood vessels in the eye; Arteriovenous malformations which is an abnormal communication between arteries and veins; Nonunion fractures which are fractures that will not heal; Lupus, and other Connective Tissue Disorders; Osler-Weber syndrome which is a genetic condition resulting in abnormal blood vessels which are prone to bleeding; Atherosclerotic plaques which is a hardening of the arteries; Psoriasis which is a common chronic skin condition; Corneal graft neovascularization which is a complication of corneal replacement surgery; Pyogenic granuloma which is a common skin lesion composed of blood vessels; Delayed wound healing; Diabetic retinopathy which is a leading cause of blindness in diabetics; Scleroderma which is a form of connective tissue disease; Granulations (burns); Neoplasm which is an abnormal cell growth forming solid tumors; Hemangioma which is a tumor composed of blood vessels; Trachoma which is a leading cause of blindness in some countries; Hypertrophic Scars which is abnormal scar formation; Retrolental fibroplasia which is abnormal growth of blood vessels in the retina; Hemophilic joints which is bleeding joints; Vascular adhesions which is excessive scarring; osteoarthritis and rheumatoid arthritis; macular degeneration; cancerous tumors generally; and pain.

Magnetism is a property of charge in motion and is related to electrical theory. As set forth in the examples, the target is mammalian tissue. A magnetic field surrounds a conductor through which current travels according to the well known "right hand rule". It is also known that a magnetic field of flux can induce current flow in circuits.

Until now, an apparatus and method capable of producing magnetic fields useful for inhibiting angiogenesis in biological subjects such as mammals was previously unknown and had not been discovered or invented.

Until now, an apparatus and method capable of producing magnetic fields useful for inhibiting angiogenesis and retarding the growth rates of cancerous tumors in biological subjects such as mammals was previously unknown and had not been discovered or invented.

SUMMARY OF THE INVENTION

An embodiment of the present invention is directed to a device for establishing or otherwise creating a substantially contained field of magnetic energy. A magnetic field produced solely by a current carrying coil can be said to constitute an electromagnetic field for purposes of this discussion. The invention and its various embodiments comprise a current carrying wire for producing a magnetic field around the wire in accordance with the well known "right hand rule" (i.e., clockwise or counterclockwise around the wire, depending upon the direction of the current flow, when viewed from a hypothetical common cross-sectional face.).

The preferred embodiments of the present invention were found useful for affecting angiogenesis and retarding the growth rates of cancerous tumors in mammals such as laboratory mice. The preferred embodiment is a coil of conductor such as a wire with a voltage drop across its opposing ends wherein the affect on angiogenesis and retardation of tumor growth has been observed to be statistically significant, as verified by independent laboratory research tests, within the area bounded by the coil (i.e., within the confines of the coil).

Tumors cannot thrive without sufficient nutrition provided by the increased circulation of blood achieved through angiogenesis. Improved wound healing may also be explained by a reduction in angiogenesis. In the wound healing process, excessive angiogenesis is believed to lead to scar formation and inefficient (and thereby slower) healing. Pharmaceutical anti-angiogenic agents have reportedly improved wound healing by limiting angiogenic activity and avoiding pathologic angiogenesis. Pathologic angiogenesis is also present in such diseases as arthritis and autoimmune diseases (such as lupus and colitis). Therefore, it is currently believed that the common effects of a magnetic field are derived by modulating the effects of transforming growth factor beta (TGFb) alone or in combination with some other cellular or ionic effect.

TGFb is involved in a number of physiological processes, including cell growth and differentiation, embryonic development, extracellular matrix formation, bone remodeling, wound healing, immune function, and angiogenesis. It is further believed that an increased expression of TGFb may mediate such activities as autoimmune disease. In addition, increased serum expression of TGFb has been shown to relieve rheumatoid arthritis symptoms.

The regulation of TGFb by the magnetic field of the present invention is explained by its varied effects of the field. It is unknown for certain, but it is believed that this regulation involves the expression of TGFb, either by itself or through the receptors for TGFb located on various target cells. Because of the magnetic and electrical elements of the field produced by the present invention and its application to a biological system, it is further believed that the receptors for TGFb provide the motive messaging to the target cells to affect TGFb. For example, the field could cause the cell to perform as though is had bound to TGFb by activating the TGFb receptors (especially the TGFb receptor 2).

Many sources cite TGFb as a protagonist of angiogenesis. Although increased expression of TGFb may be present in many cases of angiogenesis, others have shown that TGFb actually inhibits angiogenesis in microvascular endothelial cells. This effect seems to be directly linked to the activity of the TGFb receptor 2 (TGFb R2). When TGFb R2 is present and active at a ratio of approximately 5:1 with respect to the TGFb R1, proliferation of endothelial cells is inhibited. The TGFb R2 receptors are necessary to allow activation of the TGFb R1 receptor with its resulting phosphorylation cascade. The TGFb receptors are believed to be present on cell surfaces at all times, but are activated or made dormant by signals in the extracellular matrix. The expression of the magnetic field of the present invention on the extracellular matrix likely activates TGFb R2 sites to allow a phosphorylation cascade which inhibits angiogenesis.

The EMF field has major components carrying frequency harmonics of 60 hertz (i.e., frequencies at 60 Hz, 120 Hz, 240 Hz, 480 Hz, etc.). Studies have shown that the TGFb receptor reacts as though it is bound to the TGFb protein at frequencies of approximately 120 Hz. In other words, the presence of a field and its induced current at a frequency of 120 Hz is believed to cause the TGFb receptor to act as though it had been bound by TGFb. This effect would cause the same result in a biological system as an infusion or increased expression of TGFb. This frequency response, induced by the field produced by the present invention, is believed to be associated with the field's strong frequency expression at 120 Hz and its harmonics and sub-harmonics.

For example, the field at an amplitude of approximately 15–17 mT (the recommended therapeutic amplitude) should induce a voltage of approximately one to ten millivolts with a current of approximately 10 milliamps in a subject exposed to the field. This voltage and amperage are sufficient to induce a biological effect in the subject.

In addition, an effect on either the expression or reception of an angiogenic growth factor such as vascular endothelial growth factor (VEGF) or basic fibroblast growth factor (bFGF) would help explain the robust effect achieved by the field of the present invention in inhibiting angiogenesis. Based on the apparently delayed field effect on angiogenesis, the field of the present invention is also believed to affect the expression or reception of bFGF since bFGF is generally present in the later stages of tumor development.

An embodiment of the apparatus portion of the present discovery and invention includes a plurality of permanent magnets which are positioned about the periphery of a geometric frame in the form of a circle, rectangle, square or other shape such as the preferred ellipsoidal shape having a central opening. The preferred embodiment incorporates an ellipsoidal shape comprised of multiple arc length segments and therefore does not resemble a true ellipse, even though such approximations might not be detectable to the human eye.

The preferred embodiment comprises a tightly wound coil of continuous wire wrapped about a non-conductive frame, preferably made of phenolic resin impregnated spun glass fibers, in a manner similar to winding thread around a spool. A current is passed through the coil in one of two directions "+" positive or "−". negative, (i.e., to the right or to the left). The current carrying coil produces a magnetic field.

The number of coil wire turns may vary. Various embodiments of the present inventive apparatus incorporate devices using between fifty (50) and one thousand two hundred (1200) turns of insulated copper wire, because of the heat generated in the coil due to the inherent resistance of the wire to carry a current. Still other verifying studies are ongoing using devices having more or less windings than the exemplary ranges just specified (e.g., one thousand six hundred (1,600)). The coils themselves may be a single coil or multiple individual coils in a stacked or adjacent relationship where the total number of coil windings is counted.

Within the coil assembly is an optional thermal sensor or array of thermal sensors of either the resistance or thermocouple type. The sensors measure and allow quantification of the coil temperature at various points corresponding to the placement of the sensors. The optional thermal sensors, therefore, enable the operator to monitor the amount of heat generated by the device during use.

The preferred power supply incorporates a variac type transformer capable of delivering up to the preferred amperage range of 0–15 amperes of current. The corresponding voltage to achieve the 0–15 ampere range depends upon the number of turns of wire used to form the coil, but typically includes a 110 or 220 volt (i.e., 110 V or 220 V) 60 cycle (hertz or Hz) supply voltage for studies done in the United States. Other supply voltages are contemplated depending upon the nature of the electrical distribution of the locality in which the apparatus is used.

The AC input voltage applied to the coil is passed through a voltage regulating device for modulating (i.e., increasing or decreasing) the voltage as desired by the operator depending upon the application. In the alternative, where fixed voltages are used or desired, for example in the coil assembly embodiments having a large number of windings a transformer is used to provide a preselected steady state voltage (i.e., the working voltage from the variac type device) emerging therefrom. The working voltage is directed to a rectifier to convert the AC input to a DC output. The AC voltage is preferably rectified by a full-wave rectifier set.

The rectifier converts the applied AC current to a direct current (DC) with a resulting ripple frequency of either 60 cycles per second (i.e., half wave rectification) or 120 cycles per second (i.e., fill wave rectification) depending upon the rectifier setup. The harmonics of 60 cycles or 120 cycles are also believed to be useful to achieve the desired result, or they may be filtered to eliminate them and their associated affects. Similarly, where fifty (50) cycle per second current is used as the AC supply voltage, the resulting ripple frequency is either 50 or 100 cycles per second depending upon the rectification. The nature of the wave form is best described as a DC one half sine wave configuration.

The invention may be summarized in a variety of ways, one of which is the following: an apparatus for inhibiting angiogenesis and retarding the growth of cancerous tumors present in mammalian subjects, comprising means for producing a magnetic field, wherein the means includes a coil assembly including at least one electrical conductor wrapped around a frame defining a coil assembly interior; and a source of DC electrical energy for supplying a DC electrical current to the length of electrical conductor to create a magnetic field within the interior of the coil.

The at least one electrical conductor may further include a plurality of electrical conductors around the frame. The device also preferably includes an enclosure means for shielding the coil. The enclosure means consists of a side plate and a cover. The frame is substantially elliptical in shape.

With respect to the embodiments including natural magnets, a switch system capable of regulating the direction of the current flow through the coil is also provided. In the absence of natural magnets a switch means is not needed. A rectifier means for rectifying the incoming AC electrical energy is also provided. The rectifier means may provide either full wave or half wave DC rectification of a wave form associated with the DC electrical energy, and a plurality of DC bridge rectifiers may be used where the incoming AC working voltage and current is split from a single source to form a plurality of sources. In the preferred embodiment, at least one thermocouple sensor is positioned adjacent to at least one electrical conductor for measuring the temperature of the conductor.

The at least one electrical conductor is wrapped around the frame between 50 and 1600 times, and each of the plurality of electrical conductors may also be wrapped around the frame between 50 and 1600 times. The working current is preferably in the amperage range from approximately 5 amps and 10 amps, but other ranges such as between 2 and 20 amps are also believed to be useful and remain within the scope of the present invention. The present invention may also be summarized as a means for inhibiting angiogenesis and retarding the growth of cancerous tumors present in mammalian subjects, comprising a coil assembly including at least one electrical conductor wrapped around a frame defining a coil assembly interior; and a source of DC electrical energy for supplying a DC electrical current to the length of electrical conductor to create a magnetic field within the interior of the coil.

The present invention may also be summarized as an inventive apparatus capable of producing a magnetic field for retarding or inhibiting angiogenesis and the growth of cancerous tumors present in mammalian subjects, comprising a coil assembly including at least one length of electrically conducting wire wrapped about a frame which defines an interior of the coil assembly; and DC voltage means for supplying a DC electrical current to the coil assembly to create a magnetic field within the interior of the coil assembly.

The method of the present invention may also be summarized as a method of inhibiting angiogenesis and retarding the growth rate of cancerous tumors present in a mammalian subject, the method comprising the steps of: providing a device for generating a magnetic field wherein the device has a frame and a coil of wire wrapped about the frame; producing a source of DC current; connecting the source of DC current to the coil of wire; energizing the coil of wire with the DC current to create a magnetic field around the wire; and placing a biological subject having a cancerous tumor in the magnetic field to expose the biological subject to the field.

The present invention may also be summarized as follows: an apparatus for inhibiting angiogenesis and retarding the growth of cancerous tumors present in mammalian subjects, comprising means for producing a magnetic field, wherein the means includes a coil assembly including at least one electrical conductor wrapped around a frame defining a coil assembly interior; and a source of DC electrical energy for supplying a DC electrical current to the length of electrical conductor to create a magnetic field within the interior of the coil.

The at least one electrical conductor further includes a plurality of electrical conductors around the frame, and the preferred device further includes enclosure means for shielding the coil. The enclosure means comprises a side plate and a cover. A cover is removably attached to the frame to shield the coil; wherein the cover may be a cooperating cover and frame sized to establish a passage between the coil and the cover to form at least one duct to enable natural or forced gaseous (e.g., air) flow into and out of the passage from a location outside of the passage. In addition where multiple coils are used, the individual coils can be separated by a series of spacers and the like. The spacers enable air to flow in and around each individual coil winding for more efficient cooling.

The preferred frame is substantially elliptical in shape. An enclosure means for shielding the plurality of electrical conductors is also preferred. The cover may be removably attached to the frame to shield the coil, but it is preferably rigidly attached and difficult to remove. A switch device to control the direction of current flow through the coil may also be used. The rectifier means is used to rectify the incoming AC electrical energy to DC. The rectifier means provides full or half wave DC rectification of a wave form associated with the DC electrical energy, and may include a plurality of DC bridge rectifiers. An optional thermocouple sensor is positioned adjacent to the at least one electrical conductor for measuring the temperature of the conductor. The coil is wrapped about the frame preferably between 50 and 1600 turns.

The preferred embodiment may also be summarized as follows: an inventive apparatus capable of producing a magnetic field for retarding angiogenesis and the growth of cancerous tumors present in mammalian subjects, comprising a coil assembly including at least one length of electrically conducting wire wrapped about a frame which defines an interior of the coil assembly; and DC voltage means for supplying a DC electrical current to the coil assembly to create a magnetic field within the interior of the coil assembly.

The preferred embodiment may also be summarized as follows: a means for inhibiting angiogenesis and retarding the growth of cancerous tumors present in mammalian subjects, comprising a coil assembly including at least one electrical conductor wrapped around a frame defining a coil assembly interior; and a source of DC electrical energy for supplying a DC electrical current to the length of electrical conductor to create a magnetic field within the interior of the coil.

The preferred method may be summarized as follows: a method of inhibiting angiogenesis and retarding the growth rate of cancerous tumors present in a mammalian subject, the method comprising the steps of: providing a device for generating a magnetic field wherein the device has a frame and a coil of wire wrapped about the frame; producing a source of DC current; connecting the source of DC current to the coil of wire; energizing the coil of wire with the DC current to create a magnetic field around the wire; and placing a biological subject having a cancerous tumor in the magnetic field to expose the biological subject to the field.

The device for generating a magnetic field is preceded by the step of configuring an inventive device capable of generating a magnetic field with a coil of wire having 50 and 1600 turns of wire wrapped around a frame.

The step of energizing the coil of wire further comprises the step of selecting an input current in the range of between 1 amp and 15 amps and exposing the biological subject to the magnetic field for a period of time greater than 5 minutes.

It is an object of the present invention to provide a device and method for inhibiting angiogenic activity and retarding the growth rate of cancerous tumors in biological subjects including mammals.

It is an object of the present invention to provide a device and associated method for inhibiting angiogenesis and retarding cancerous tumor growth in biological subjects including mammals.

It is an object of the present invention to provide a device and method capable of inhibiting angiogenic related conditions and retarding cancerous tumor growth in biological subjects including mammals.

It is an object of the present invention to provide a device and method for slowing or inhibiting the rate of angiogenesis and cancerous tumor growth in biological subjects including mammals.

It is an object of the present invention to provide an electrical device and method for inhibiting angiogenic activity and retarding cancerous tumor growth in biological subjects including mammals.

It is an object of the present invention to provide an electrical device and associated method for inhibiting angiogenesis and retarding cancerous tumor growth in biological subjects including mammals.

It is an object of the present invention to provide an electrical device and method capable of inhibiting angiogenic related conditions and retarding cancerous tumor growth in biological subjects including mammals.

It is an object of the present invention to provide an electrical device and method for slowing or inhibiting the rate of angiogenesis and retarding cancerous tumor growth in biological subjects including mammals.

It is an object of the present invention to provide a method and/or apparatus for affecting the following as they relate to angiogenesis: Angiofibroma which is an abnormal formation of blood vessels which are prone to bleeding; Neovascular Glaucoma which is an abnormal growth of blood vessels in the eye; Arteriovenous malformations which is an abnormal communication between arteries and veins; Nonunion fractures which are fractures that will not heal; Lupus, and other Connective Tissue Disorders; Osler-Weber syndrome which is a genetic condition resulting in abnormal blood vessels which are prone to bleeding; Atherosclerotic plaques which is a hardening of the arteries; Psoriasis which is a common chronic skin condition; Corneal graft neovascularization which is a complication of corneal replacement surgery; Pyogenic granuloma which is a common skin lesion composed of blood vessels; Delayed wound healing; Diabetic retinopathy which is a leading cause of blindness in diabetics; Scleroderma which is a form of connective tissue disease; Granulations (burns); Neoplasm which is an abnormal cell growth forming solid tumors; Hemangioma which is a tumor composed of blood vessels; Trachoma which is a leading cause of blindness in some countries; Hypertrophic Scars which is abnormal scar formation; Retrolental fibroplasia which is abnormal growth of blood vessels in the retina; Hemophilic joints which is bleeding joints; Vascular adhesions which is excessive scarring; osteoarthritis and rheumatoid arthritis; macular degeneration; cancerous tumors generally; and pain.

These and other objects, features, and advantages of the present invention shall become apparent after consideration of the invention as defined above in conjunction with the disclosure provided herein, including the specification, drawings, and claims. All such objects, features and advantages are believed to be within the scope of the present invention even though not specifically set forth in this document.

BRIEF DESCRIPTION OF THE DRAWINGS

Figure A is a schematic diagram of the cells of a blood carrying vessel;

Figure B is a schematic diagram similar to that of Figure A and including information relating to the initiation of angiogenesis;

Figure 1A:
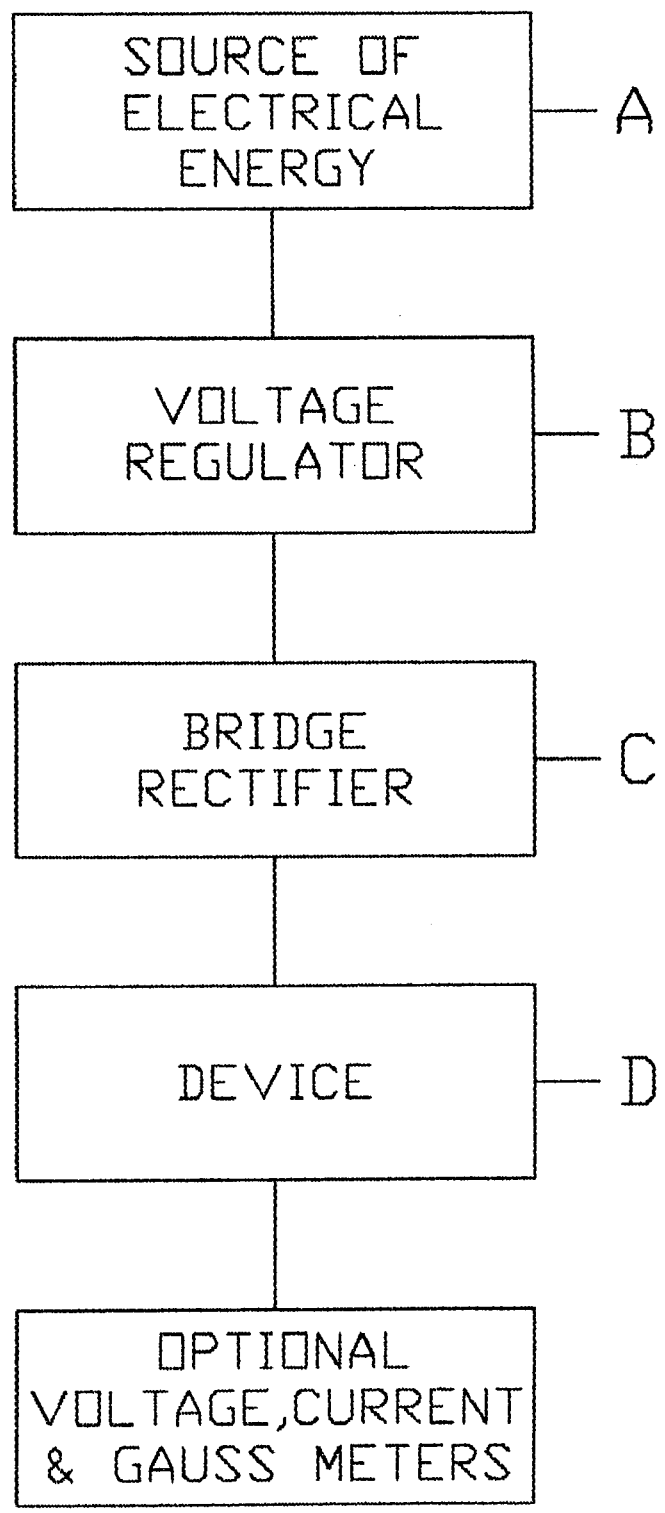
Figure 1B:
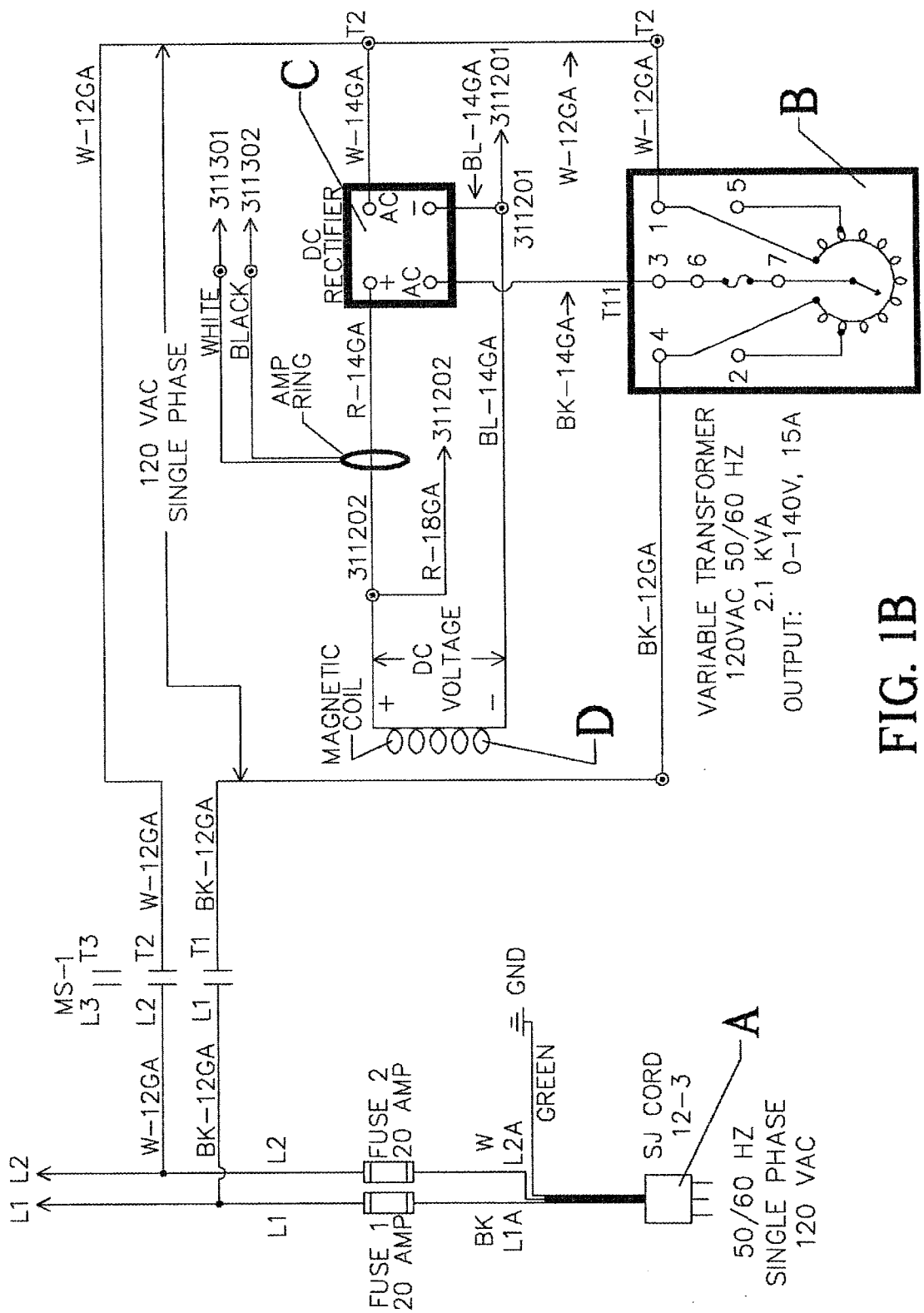

Figure C is a schematic diagram similar to Figures A and B and including information relating to an advanced stage of angiogenesis sometime after the process was initiated;

FIGS. 1A and 1B are schematic block diagrams of the electrical components of the present invention;

FIG. 2 is an illustration of the relative orientation of the magnetic components and coil component of an embodiment of the present invention;

FIG. 3 is a cross-sectional view taken along line A—A of FIG. 2;

FIG. 4 is side view of the preferred embodiment of the present invention;

FIG. 5 is a cross-sectional view of the preferred embodiment taken along line A—A of FIG. 4.

Figure 6:
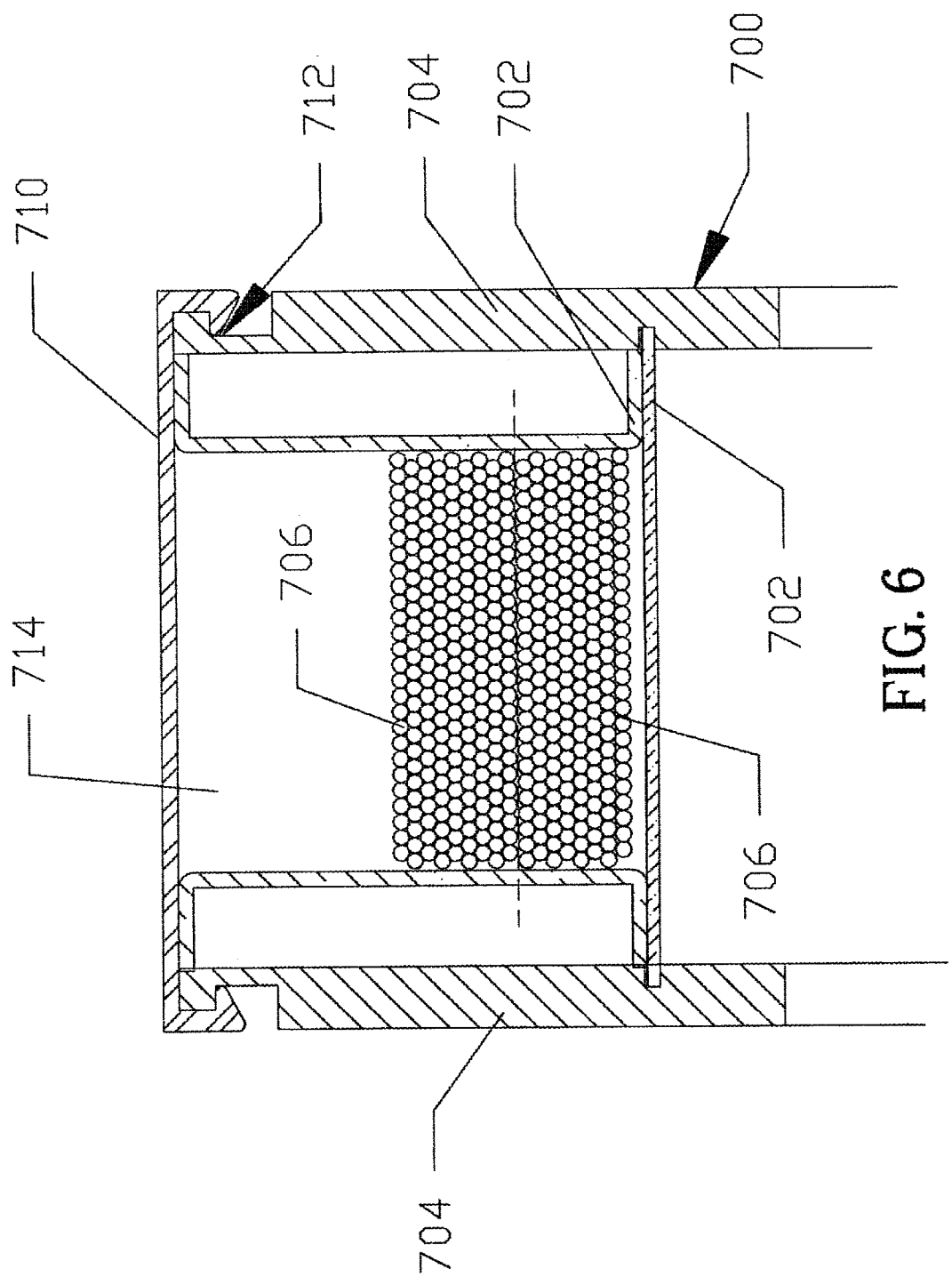
Figures 7, 8, 9:
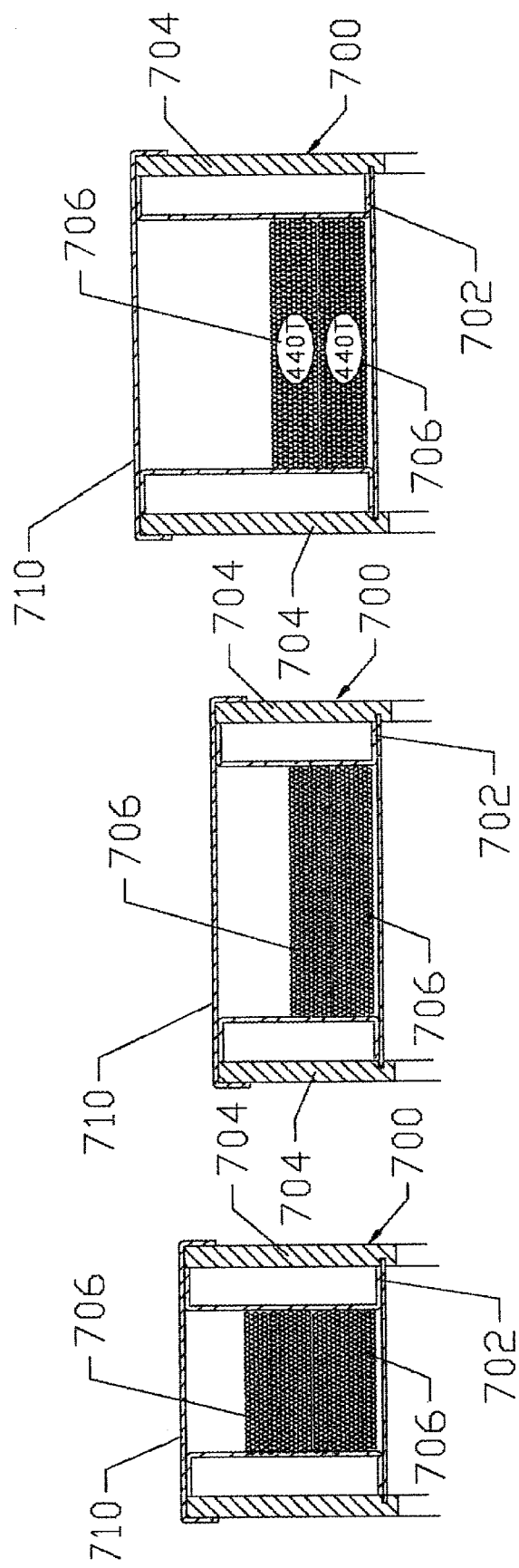
Figure 10:
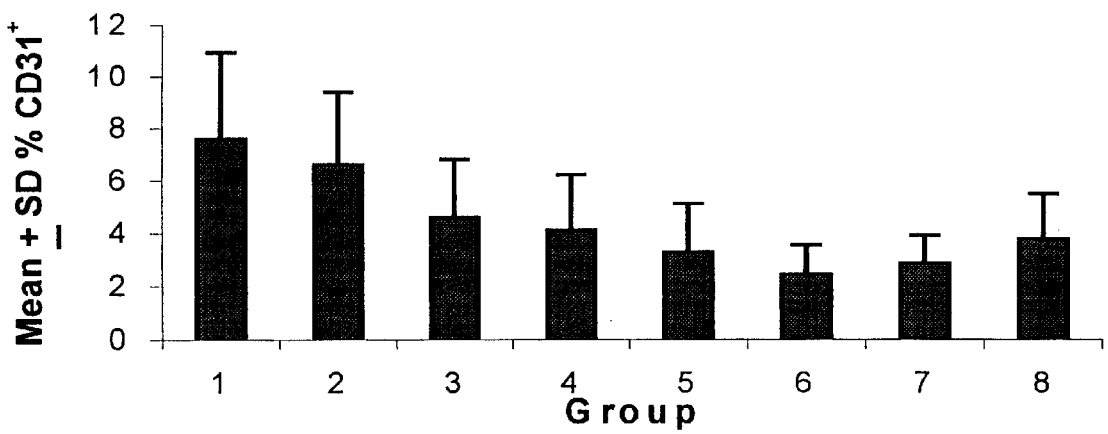
Figure 11:
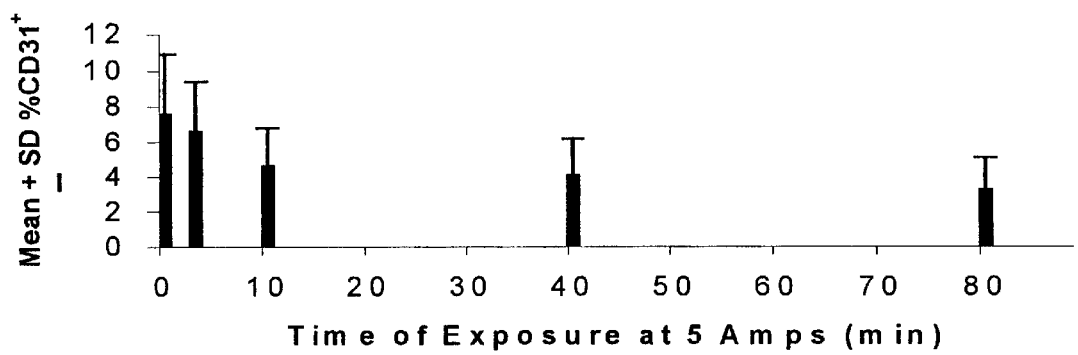
Figure 12:
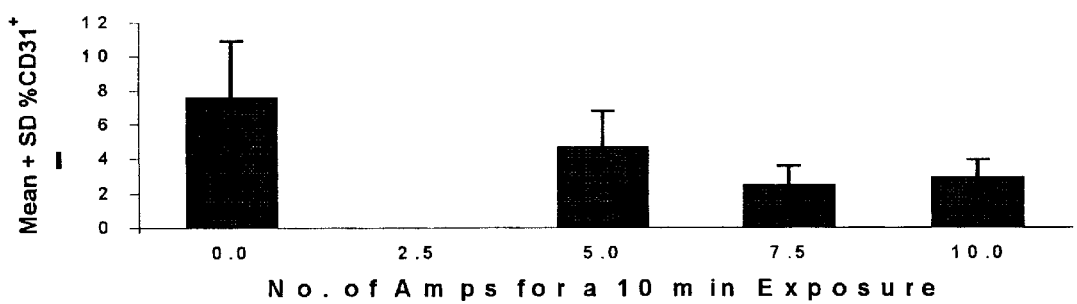
Figure 13:
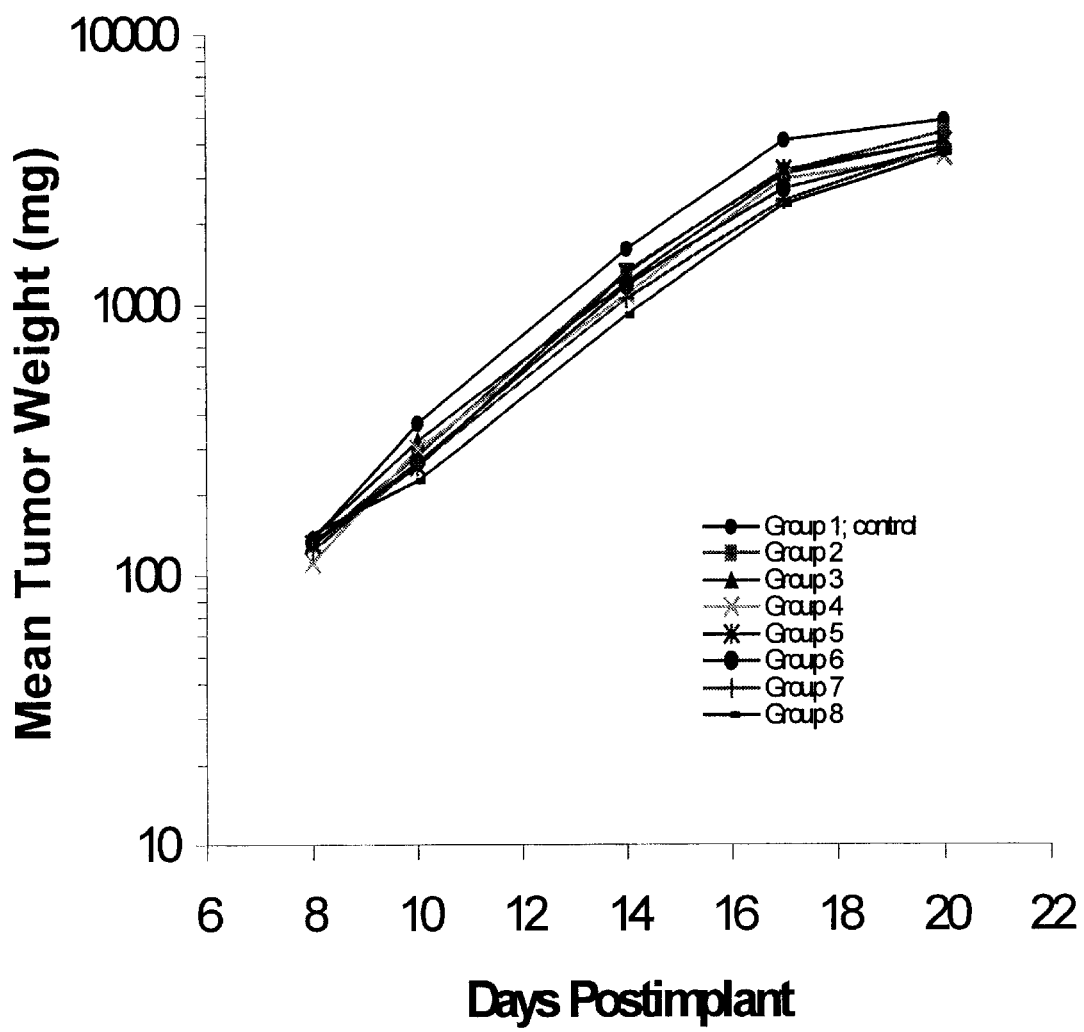
Figure 14:
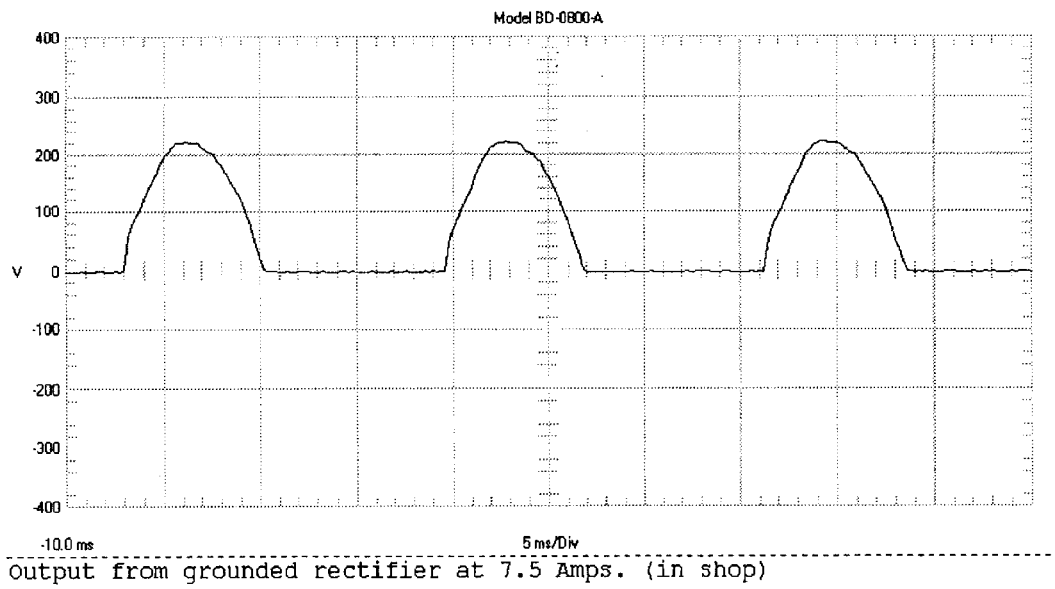
Figure 15:
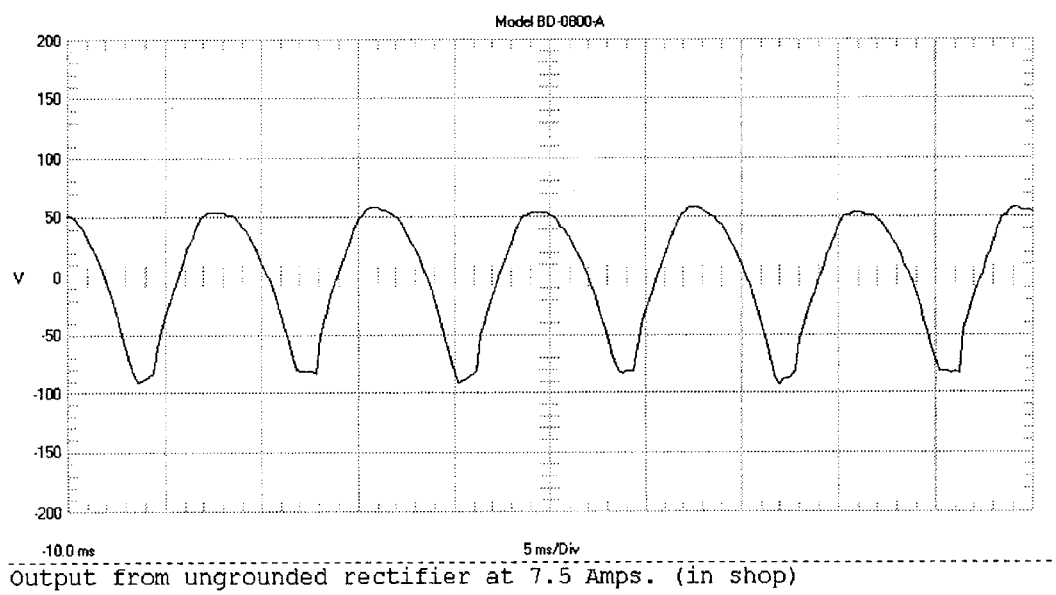
Figure 16:
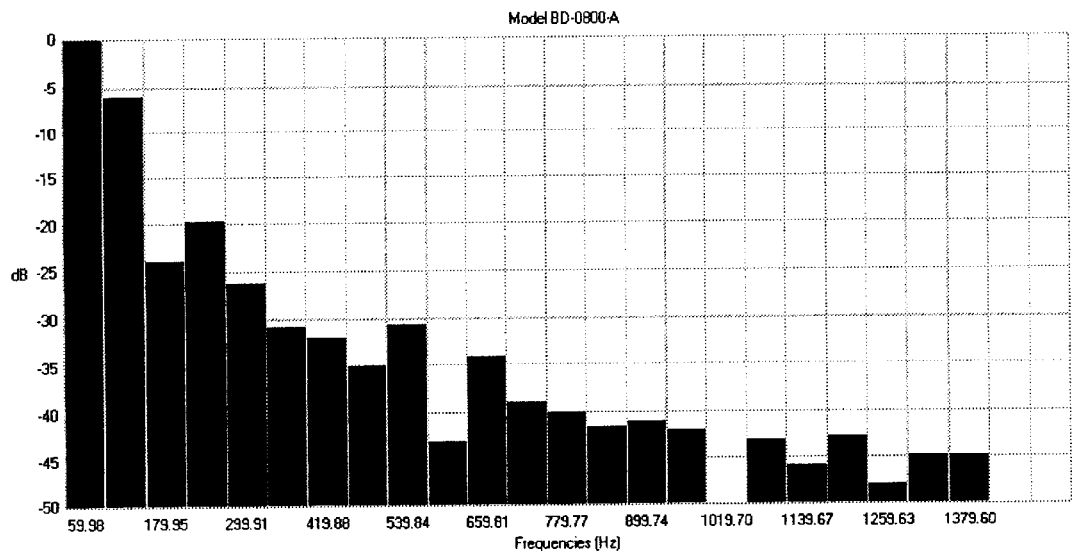
Figure 17:
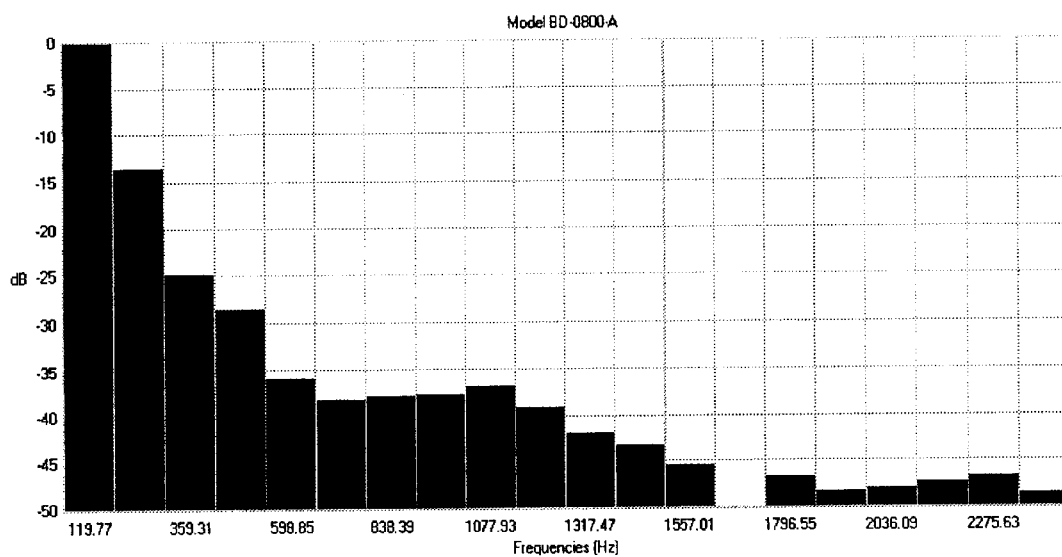

FIG. 6 is an enlarged sectional view of the portion of the preferred embodiment bounded by the viewing circle of FIG. 5 and further including a cover component;

FIGS. 7–9 are alternate embodiments of the present invention shown in FIG. 6;

FIG. 10 is a bar graph titled "Angiogenesis Assessment in 16/C [Mammary] Tumors"—Groups 1–8;

FIG. 11 is a bar graph titled "Angiogenesis Assessment in 16/C [Mammary] Tumors—Groups 1–5";

FIG. 12 is a bar graph titled "Angiogenesis Assessment in 16/C [Mammary] Tumors—Groups 1, 3, 6 and 7"; and FIG. 13 is a line graph titled "Response of SC 16/C Mammary Tumor to Exposure to Electromagnetic Fields"; and FIG. 14 is a graph illustrating the half rectified wave form produced by an embodiment of the present invention; and FIG. 15 is a graph illustrating the fully rectified wave form produced by an embodiment of the present invention; and FIG. 16 is a bar graph illustrating the harmonic range of the wave form illustrated in FIG. 14; and FIG. 17 is a bar graph illustrating the harmonic range of the wave form illustrated in FIG. 15.

DETAILED DESCRIPTION OF THE PREFERRED EMBODIMENT(S)

With reference to the schematic diagrams designated as FIGS. 1A and 1B, a source of electrical energy, preferably 110 or 220 volts in the United States, is designated generally by the reference letter A. An AC transformer, designated generally by the reference letter B and labeled "power supply", is electrically connected to the source A by a conventional power cord preferably rated to handle the input voltage of the source.

The transformer varies the AC input voltage. The AC output is then passed through a single or series of bridge rectifiers C. The bridge rectifiers preferably provide either a full wave or half wave rectification of the wave form to a 60 or 120 cycles per second DC "positive" (i.e., above the reference line on a sinusoidal oscilloscope) wave form. The fully rectified wave form from the bridge rectifier(s) is then passed to the free ends of the coil designated generally by the reference letter D and labeled "DEVICE" for convenience. With reference to FIGS. 1B and 1C, an electrical schematic of the system is provided.

FIGS. 14 and 15 are graphs illustrating the half rectified and fully rectified, respectively, wave form produced by an eight hundred (800) winding embodiment of the present invention. The sample graphs were taken when the field strength within the confines of the embodiment tested was set to produce 7.5 amps of current. FIGS. 16 and 17 illustrate the harmonics corresponding to the wave forms of FIGS. 14 and 15 respectively.

With reference to FIGS. 2 and 3, an embodiment of the device component of the present invention is designated generally by the reference number 600. The device frame 602 has been partially removed from FIG. 2 in order to show the permanent magnets 604 and the interiorly wrapped coil 606 in their preferred orientation. The coil winding 606 overlies the belt or annular layer of permanent magnets 604. A cover 610 is provided as a means of protecting and shielding the coil 606 during operation.

Within the coil assembly are a plurality of optional thermal sensors (not shown in FIGS. 2 and 3), of either resistance or thermocouple type which measure and indicate the coil temperature at various points. A preferred embodiment of the sensors are manufactured by Honeywell/Microswitch, Inc. and have model number SS94A2.

Cover 610 can be a section of raceway cover which includes a cooperating tongue and groove snap connection 612 so that the cover may be removed to service the interior magnetic and coil components of the device. As such, the existence of the cover attached to the device frame 602 and the disposition of the magnet and coil establish an air space 614 between the coil 606 and cover 610. The air space 614 provides a means of convective heat transfer such that if an air flow in the air space 614 were created, the flow of air would have a tendency to cool the coil 606 and magnets 604 when they become heated after the coil 606 in energized in the manner described below.

The orientation of the coil 606 and the magnets 604 is readily observed. Cross-section line A—A, which also serves as a vertical axis and horizontal line L, which serves as a horizontal axis, define the centroid of the interior channel 620 of the device. As shown in FIG. 2, there are a pair of gaps 622 in the annular layer or belt of magnets 604. The gaps are provided so as to establish an open circuit condition so that the magnets themselves which are typically made of some metal do not become conductors. They are also believed to provide an oscillating or pulsating (i.e., changing) magnetic field as a function of time.

With reference to FIGS. 4–5, the preferred embodiment of the coil assembly of the present invention is designated generally by the reference numeral 700. Embodiment 700 includes a frame component 702. The side plates 704 (see FIGS. 3–7) cover the coil 706 as it is wrapped around the frame 702. One of the side plates has been removed from FIG. 2 for visual clarity of the coil 706 but the side plates 704 are preferably rigidly attached to the frame 702 in a working embodiment of the invention.

Within the coil assembly 704 are a plurality of optional thermal sensors 708, of either the resistance or thermocouple type. The sensors are provided as a way of measuring the coil temperature at various points but do not affect the operation of the invention and its useful effect (i.e., angiogenesis and growth retardation of cancerous tumors). The preferred sensors are manufactured by Honeywell/Microswitch, Inc. and have model number SS94A2.

A cover 710 is preferably rigidly secured to the frame. Attachment of the cover 710 to the frame 702 in the manner shown in the figures creates an air space 714 between the coil 706 and cover 710. The cover 710 may be snapped in place by a snap fit cooperation of the cover and the frame 712, or I the alternative the cover may be rigidly and securely attached by numerous others means of securement. The air space 714 allows for convective heat transfer from the coil 706 to the air within the air space 714. If an air flow is induced in the air space 714, the flow of air would have a s tendency to cool the coil 706 if it heats up during use.

With reference to FIGS. 5 and 6, the orientation of the frame 702, the side plates 704 and the coil 706, are readily observed. Cross-section line A—A of FIG. 4, which also serves as a vertical axis V intersects the horizontal axis H to define the interior centroid of the interior 716 of the device (FIG. 4). When a current flow is induced into the coil 706, a magnetic field around the coil is established pursuant to the right hand rule. The magnetic lines of flux (not shown) are either to the left or to the right depending upon the frame of reference and the direction of current flow in the coil 706.

FIGS. 6–9 illustrate a variety of device profiles in order to demonstrate the various configurations the coil 706 may have depending upon the width of the frame. As shown in FIGS. 6 and 9, the device may also multiple coils 706 in a stacked or adjacent relationship as denoted by the hypothetical dashed dividing line of those figures. An optimum coil thickness with respect to width is believed to help establish a more uniform minimum heat generation within the coil 706. It is contemplated that a coil cross-section like that shown in FIGS. 5–9 is optimum when the heat generated by the coil is at a minimum, and trial and error tests are expected to support this contention.

A MODE OF OPERATION

The use of the inventive apparatus for inhibiting angiogenesis can be best described in conjunction with a series of examples with supporting data that are set forth below.

Consideration of the known biological attributes of a healthy mammalian body were relied upon as known information for the experiments. All laboratory tests and experiments were performed on laboratory mice with active malignant cancer cells in an independent research laboratory facility and setting for affirmation. The intent of the experiments was to analyze the effectiveness of the inventive apparatus and method whose net intended result was proven to have an affect to inhibit the normal expected rate of angiogenesis and retard cancerous tumor growth.

The following examples, therefore, set forth representative data obtained from some of the experiments and tests which were all conducted in a confidential, controlled setting. The procedure used for the mammalian animal tests can best be described as follows:

The device and a cooling fan to provide air flow in the air space were connected to a standard 110 V or 220 V electrical service. The device was allowed to warm up through one ten-minute cycle (either positive or negative direction on current flow through coil component). The input current level was adjusted to ten amps during warm up and adjusted periodically to maintain a steady state ten (10) amperes supply current. The net result, depending upon a positive direction or negative direction of current flow was a magnetic field generated from the coil combined with the background magnetic field associated with the magnets.

After warm up, the first animal subjects (i.e., laboratory mice of defined lineage) were placed onto a non-metallic shelf within the generated field. The operator selected a positive or negative direction of current flow through the coil component, as appropriate. The ten (10) amperes of supply current was verified and adjusted if necessary. Periodic checks were performed to maintain ten (10) amps.

A simple current timer as used at the outlet to cut power at the expiration of ten minutes exposure of the subjects to the combined magnetic field. After ten minutes, the device was designed to automatically shut down. The first group of exposed subjects were then removed, placed back in their respective cages and the exposure was performed again and repeated with the next group until all of the subjects were exposed to either a positive or a negative combined field (depending upon the direction of current flow in the coil component), excepting the control animals which received no exposure to the combined field in any way. Measurements of tumor size and animal handling were conducted in accordance with the research facility protocol.

Twenty (20) control mice and ten (10) mice in each of the treatment groups (i.e., positive and negative direction of current flow through the coil component). All of the mice were selected from a single lineage as good laboratory and experimental practices dictate. Each mouse was implanted with "16/C mammary adenocarcinoma" which is known to be a fast growing "aggressive" tumor model. The treatment began when the median tumor weights reached 100 mg. The treatments were terminated when the tumors became too large to allow the study to continue due to humane considerations (approximately two weeks of treatment).

At the conclusion of the experiment, the mice were sacrificed and the tumors were analyzed by preparing cross-sectional tumor slides from 3 mice per cage Group (i.e., 3 control, 3 positive, and 3 negative). For each tumor, the independent researcher examined 5 sites on the slide to quantitate it for CD31 staining—a known standard of cellular staining. The data is reported in EXAMPLE ONE below.

STUDY 1—EXAMPLE ONE

Angiogenesis Assessed by CD31 Immunohistochemistry and Image Analysis in Murine 16/C Mammary Adenocarcinoma-Bearing C3H/HeJ Mice % CD31 + Comparison by Slides (sample of preliminary data)

| Sample | Site 1 | Site 2 | Site 3 | Site 4 | Site 5 | MEAN % | STD. DEV. |
|---|---|---|---|---|---|---|---|
| Cage Group 1-1 | 28.88 | 21.17 | 24.04 | 18.27 | 11.76 | 20.82 | 6.40 |
| Cage Group 1-2 | 30.09 | 18.49 | 11.38 | 19.50 | 18.32 | 19.56 | 6.72 |
| Cage Group 1-8 | 15.27 | 13.39 | 30.01 | 33.18 | 22.01 | 22.77 | 8.74 |
| Cage Group 2-2 | 8.81 | 9.04 | 20.27 | 12.65 | 12.08 | 12.57 | 4.64 |
| Cage Group 2-4 | 11.53 | 12.07 | 16.07 | 21.23 | 15.60 | 15.23 | 4.49 |
| Cage Group 2-5 | 8.59 | 10.08 | 26.53 | 28.30 | 18.50 | 18.40 | 9.08 |
| Cage Group 3-4 | 8.07 | 6.98 | 14.63 | 7.06 | 10.01 | 9.35 | 3.19 |
| Cage Group 3-7 | 8.62 | 21.48 | 9.85 | 4.24 | 10.05 | 10.85 | 6.39 |
| Cage Group 3-10 | 24.28 | 4.69 | 4.62 | 10.41 | 10.68 | 10.94 | 8.02 |

Data Analysis

By t-test,

Group 1 vs. Group 2, p=0.0280

Group 1 vs. Group 3, p<0.0001

Group 2 vs. Group 3, p=0.0128

CD31 + Comparison by Cage Groups
Micro-vessel Density Assessed by CD31 Immunohistochemistry and Image Analysis

| Sample | Treatment | MEAN % | STD. DEV. |
|---|---|---|---|
| Group 1 | None | 21.05 | 1.62 |
| Group 2 | Opposing | 15.40 | 2.92 |
| Group 3 | Additive | 10.38 | 0.89 |

"Additive" and "Opposing" refer to the orientation of the magnetic field line of flux associated with the permanent magnets and electromagnetic field lines from the coil by itself such that additive refers to an overlapping of the field lines while opposing refers to oppositely directed field lines.

STUDY 2—EXAMPLE TWO

Angiogenesis Assessed by CD31 Immunohistochemistry and Image Analysis in Human A549 Lung Carcinoma-Bearing Athymic Mice Data Analysis By t-test, Group 1 vs. Group 2, p<0.0001

Group 1 vs. Group 3, p<0.0001

Group 2 vs. Group 3, p<0.0007

CD31 + Comparison by Cage Groups
Micro-vessel Density Assessed by CD31 Immunohistochemistry and Image Analysis

| Sample | Treatment | MEAN % | STD. DEV. |
|---|---|---|---|
| Group 1 | None | 22.94 | 4.15 |
| Group 2 | Opposing | 14.05 | 2.49 |
| Group 3 | Additive | 10.23 | 2.18 |

"Additive" and "Opposing" refer to the orientation of the magnetic field line of flux associated with the permanent magnets and electromagnetic field lines from the coil by itself such that additive refers to an overlapping of the field lines while opposing refers to oppositely directed field lines.

STUDY 3—EXAMPLE THREE
Angiogenesis Assessed by CD31 Immunohistochemistry and Image Analysis in Murine 16/C Mammary Adenocarcinoma-Bearing C3H/HeJ Mice

| Micro-vessel Density Assessed by CD31 Immunohistochemistry and Image Analysis | | | |
|---|---|---|---|
| Sample | Treatment | MEAN % | STD. DEV. |
| Group 1 | None | 18.67 | 2.28 |
| Group 2 | Natural Field | 17.37 | 2.80 |
| Group 3 | electromagnetic field only | 12.27 | 2.03 |
| Group 4 | natural and electromagnetic | 15.81 | 1.21 |

Group 1 was the control group of tumor laden mice. They received no treatment but underwent the same standard care and handling as the other mice. Group 2 mice received exposure to fields generated by natural magnets only. Group 3 mice received exposure to electromagnetic fields only. Group 4 mice received exposure to a combined natural and magnetic field in an additive combination. "Additive" refers to the orientation of the magnetic field line of flux associated with the permanent magnets and electromagnetic field lines from the coil by itself such that corresponding fields overlapped.

STUDY 4—EXAMPLE FOUR
Angiogenesis Assessed by CD31 Immunohistochemistry and Image Analysis in Murine 16/C Mammary Adenocarcinoma-Bearing C3H/HeJ Mice The C3H mice in this example were implanted with murine 16/C mammary adenocarcinoma tumor cells. A control group (i.e., Group 1) of twenty mice was used. The mice in the control Group 1 were not treated with the inventive apparatus. Seven additional groups of ten mice each (Groups 2–8) were used for treatment.

Animals in Group 2 were placed within the interior of the device once daily for 3 minutes per day for 12 days beginning on day 8 following tumor implantation with the DC current at 5 amps.

Animals in Group 3 were placed within the interior of the device once daily for 10 minutes per day for 12 days beginning on day 8 following tumor implantation with the DC current at 5 amps.

Animals in Group 4 were placed within the interior of the device once daily for 40 minutes per day for 12 days beginning on day 8 following tumor implantation with the DC current at 5 amps.

Animals in Group 5 were placed within the interior of the device twice daily, at approximately 7 hour intervals) for 40 minutes for 12 days beginning on day 8 following tumor implantation with the DC current at 5 amps.

Animals in Group 6 were placed within the interior of the device once daily for 10 minutes per day for 12 days beginning on day 8 ; following tumor implantation with the DC current at 7.5 amps.

Animals in Group 7 were placed within the interior of the device once daily for 10 minutes per day for 12 days beginning on day 8 following tumor implantation with the DC current at 10 amps.

Animals in Group 8 were placed within the interior of the device twice daily, at approximately 7 hour intervals, for 10 minutes per day for 12 days beginning on day 8 following tumor implantation S with the DC current at 10 amps.

During the study tumor weight was measured periodically and consistently to determine relative growth rates. Because of the shear volume of raw data relating to %CD31+ angiogenesis assessment and tumor weight, graphical representation of the data will be used in this example instead of the tabular format used above. At the conclusion of the study the excised tumors were packed in the appropriate solution and frozen for further analysis.

With reference to FIGS. 10–13, it is clearly shown the tumors of the control group (i.e., Group 1) mice exhibited a more angiogenesis than any of the treated groups. It also appears that the Group 6 treated mice exhibited the least angiogenesis of any group and thus the preferred method of exposure for this invention, as it relates to duration, current level and time of exposure is that which is associated with the Group 6 treatment protocol. FIG. 13 also shows the tumors of the mice of the treated groups grew more slowly and thus weighed less than the tumors of the control group (i.e., Group 1) mice.

What is claimed is:

1. An apparatus for inhibiting angiogenesis and retarding the growth of cancerous tumors present in mammalian subjects, comprising:
   means for producing a magnetic field, wherein the means includes:
   a coil assembly including at least one electrical conductor wrapped around a frame defining a coil assembly interior and a central passageway extending therethrouqh; and
   a source of DC electrical energy for supplying a DC electrical current to the length of electrical conductor to create a magnetic field capable of inhibiting angiogenesis and retarding the growth of cancerous tumors Present in mammalian subjects within the interior of the coil.

2. The device of claim 1, wherein the at least one electrical conductor further includes:
   a plurality of electrical conductors.

3. The device of claim 1, further includes:
   enclosure means for shielding the coil.

4. The device of claim 3, wherein the enclosure means comprises:
   a side plate and a cover.

5. The device of claim 1 further comprising:
   a frame having a substantially elliptical shape.

6. The device of claim 2, further including:
   enclosure means for shielding the plurality of electrical conductors.

7. The device of claim 5, further including:
   a cover removably attached to the frame to shield the coil.

8. The device of claim 1, further including:
   a switch system capable of regulating the direction of the current flow through the coil.

9. The device of claim 1, such that:
   rectifier means for rectifying the incoming AC electrical energy to DC.

10. The device of claim 9, such that:
    the rectifier means provides full wave DC rectification of a wave form associated with the DC electrical energy.

11. The device of claim 9, wherein the rectifier means further comprises:
    a plurality of DC bridge rectifiers.

12. The device of claim 11, wherein:
    the plurality of DC bridge rectifiers provide full wave DC rectification.

13. The device of claim 1, further including:
    at least one thermocouple sensor positioned adjacent to the at least one electrical conductor for measuring the temperature of the conductor.

14. The device of claim 5, wherein:
the at least one electrical conductor is wrapped around the frame between 50 and 1600 times.

15. The device of claim 2, wherein:
each of the plurality of electrical conductors is wrapped around a frame between 50 and 1600 times.

16. An inventive apparatus capable of producing a magnetic field for retarding angiogenesis and the growth of cancerous tumors present in mammalian subjects, comprising:
a coil assembly including at least one length of electrically conducting wire which defines an interior of the coil assembly; and
DC voltage means for supplying a DC electrical current to the coil assembly to create a magnetic field capable of inhibiting angiogenesis and retarding the growth of cancerous tumors present in mammalian subjects within the interior of the coil assembly.

17. The device of claim 16, wherein the at least one length of electrically conducting wire further includes:
a plurality of individual wires.

18. The device of claim 16, further includes:
enclosure means for shielding the wire.

19. The device of claim 18, wherein the enclosure means comprises:
a side plate and a cover.

20. The device of claim 16 further comprising:
a frame which is substantially elliptical in shape.

21. The device of claim 17, further including:
enclosure means for shielding the plurality of individual wires.

22. The device of claim 20, wherein the enclosure means further comprises:
a cover removably attached to the frame to shield the coil.

23. The device of claim 16, such that:
a switch system capable of regulating the direction of the current flow through the wire.

24. The device of claim 16, such that:
rectifier means for rectifying a wave form associated with the incoming DC electrical current.

25. The device of claim 24, such that:
the rectifier means provides full wave DC rectification.

26. The device of claim 24, wherein the rectifier means further comprises:
a plurality of DC bridge rectifiers.

27. The device of claim 26, wherein:
the plurality of DC bridge rectifiers provide full wave DC rectification.

28. The device of claim 20, wherein:
the at least one electrically conducting wire is wrapped around the frame between 50 and 1600 times.

29. The device of claim 17, wherein:
each of the plurality of electrically conducting wires is wrapped around a frame between 50 and 1600 times.

30. The device of claim 16, further including:
at least one thermocouple sensor positioned adjacent to the at least one electrically conducting wire for measuring a temperature of the conductor.

31. A means for inhibiting angiogenesis and retarding the growth of cancerous tumors present in mammalian subjects, comprising:
a coil assembly including at least one electrical conductor defining a coil assembly interior including a passageway; and
a source of DC electrical energy for supplying a DC electrical current to the length of electrical conductor to create a magnetic field capable of inhibiting angiogenesis and retarding the growth of cancerous tumors present in mammalian subjects within the interior of the coil and the passageway.

32. The device of claim 31, wherein the at least one electrical conductor further includes:
a plurality of electrical conductors.

33. The device of claim 31, further includes:
enclosure means for shielding the coil.

34. The device of claim 33, wherein the enclosure means comprises:
a side plate and a cover.

35. The device of claim 33 further comprising:
a frame which is substantially elliptical in shape.

36. The device of claim 32, further including:
enclosure means for shielding the plurality of electrical conductors.

37. The device of claim 35, further including:
a cover removably attached to the frame to shield the coil.

38. The device of claim 31, further including:
a switch system capable of regulating the direction of the current flow through the coil.

39. The device of claim 31, such that:
rectifier means for rectifying the incoming DC electrical energy.

40. The device of claim 39, such that:
the rectifier means provides full wave DC rectification of a wave form associated with the DC electrical energy.

41. The device of claim 39, wherein the rectifier means further comprises:
a plurality of DC bridge rectifiers.

42. The device of claim 41, wherein:
the plurality of DC bridge rectifiers provide full wave DC rectification.

43. The device of claim 35, wherein:
the at least one electrical conductor is wrapped around the frame between 50 and 1600 times.

44. The device of claim 32, wherein:
each of the plurality of electrical conductors is wrapped between 50 and 1600 times.

45. The device of claim 31, further including:
at least one thermocouple sensor positioned adjacent to the at least one electrical conductor for measuring a temperature of the conductor.

46. A method of inhibiting angiogenesis and retarding the growth rate of cancerous tumors present in a mammalian subject, the method comprising the steps of:
providing a device for generating a magnetic field wherein the device includes a coil of wire;
producing a source of DC current;
connecting the source of DC current to the coil of wire;
energizing the coil of wire with the DC current to create a magnetic field around the wire;
producing a magnetic field capable of inhibiting angiogenesis and retarding the growth of cancerous tumors present in mammalian subjects; and
placing a biological subject having a cancerous tumor in the magnetic field to expose the biological subject to the field.

47. The method of claim 46, wherein the step of providing a device for generating a magnetic field is preceded by the step of:

configuring a device capable of generating a magnetic field with a coil of wire having between 50 and 1600 turns of wire wrapped around a frame.

48. The method of claim 46, wherein the step of energizing the coil of wire further comprises the step of:

selecting an input current in the range of between 1 amp and 15 amps.

49. The method of claim 46, further comprising the step of:

exposing the biological subject to the magnetic field for a period of time greater than 5 minutes.

\* \* \* \* \*